United States Patent
Funakoshi et al.

(10) Patent No.: US 9,758,703 B2
(45) Date of Patent: Sep. 12, 2017

(54) TACKIFIER, TACKIFIER FOR MEDICAL OR INDUSTRIAL USE, ADHESIVE AND/OR PRESSURE-SENSITIVE ADHESIVE FOR MEDICAL OR INDUSTRIAL USE, ADHESIVE SHEET AND/OR PRESSURE-SENSITIVE ADHESIVE SHEET FOR MEDICAL OR INDUSTRIAL USE, AND PRESSURE-SENSITIVE ADHESIVE TAPE FOR MEDICAL OR INDUSTRIAL USE

(71) Applicant: ARAKAWA CHEMICAL INDUSTRIES, LTD., Osaka (JP)

(72) Inventors: Yasushi Funakoshi, Osaka (JP); Takashi Nakatani, Osaka (JP)

(73) Assignee: ARAKAWA CHEMICAL INDUSTRIES, LTD., Osaka (JP)

( * ) Notice: Subject to any disclaimer, the term of this patent is extended or adjusted under 35 U.S.C. 154(b) by 126 days.

(21) Appl. No.: 14/374,188

(22) PCT Filed: Jan. 25, 2013

(86) PCT No.: PCT/JP2013/051662
§ 371 (c)(1),
(2) Date: Jul. 23, 2014

(87) PCT Pub. No.: WO2013/111883
PCT Pub. Date: Aug. 1, 2013

(65) Prior Publication Data
US 2015/0032042 A1    Jan. 29, 2015

(30) Foreign Application Priority Data
Jan. 28, 2012  (JP) ................. 2012-016006

(51) Int. Cl.
| C08K 5/11 | (2006.01) |
| C09J 109/06 | (2006.01) |
| C09J 121/00 | (2006.01) |
| C09J 193/04 | (2006.01) |
| C08K 5/103 | (2006.01) |
| C09J 153/00 | (2006.01) |
| A61L 15/58 | (2006.01) |

(52) U.S. Cl.
CPC ........... C09J 109/06 (2013.01); A61L 15/585 (2013.01); C08K 5/103 (2013.01); C08K 5/11 (2013.01); C09J 121/00 (2013.01); C09J 153/00 (2013.01); C09J 193/04 (2013.01)

(58) Field of Classification Search
CPC ...... C09J 109/06; C09J 121/00; C09J 193/04; C09J 153/00; C08K 5/11; C08K 5/103; A61L 15/58; A61L 15/585; C08L 53/02
USPC .................... 524/113, 270; 602/54; 106/505
See application file for complete search history.

(56) References Cited

U.S. PATENT DOCUMENTS 5,395,920 A    3/1995  Maeda et al.

FOREIGN PATENT DOCUMENTS

| CN | 101397479 A | 4/2009 |
| JP | H01-161078 A | 6/1989 |
| JP | 1993279631 | 10/1993 |
| JP | H08-157789 A | 6/1996 |
| JP | 2005170833 A | 6/2005 |
| JP | 2009084421 A | 4/2009 |
| JP | 2009161573 A | 7/2009 |
| JP | 2009209178 A | 9/2009 |

OTHER PUBLICATIONS

International Preliminary Report on Patentability in corresponding PCT/JP2013/051662 dated Jul. 29, 2014. (English Translation).
International Search Report in corresponding PCT/JP2013/051662 dated Apr. 23, 2013.
Written Opinion in corresponding PCT/JP2013/051662 dated Apr. 23, 2013.

Primary Examiner — Josephine Chang
(74) Attorney, Agent, or Firm — Marshall, Gerstein & Borun LLP

(57) ABSTRACT

Provided is a resin acid ester-based tackifier having a good compatibility with a synthetic rubber elastomer, being capable of reducing the melt viscosity of the elastomer, and being capable of imparting excellent adhesive properties and/or pressure-sensitive adhesive properties to the elastomer.

$$Ro-\overset{O}{\overset{\|}{C}}-O-R-O-\overset{O}{\overset{\|}{C}}-Ro \quad (1)$$
$$\overset{|}{\underset{\|}{O}}-\overset{}{\underset{\|}{C}}-Ro$$
$$\overset{}{\underset{}{O}}$$

7 Claims, No Drawings

TACKIFIER, TACKIFIER FOR MEDICAL OR INDUSTRIAL USE, ADHESIVE AND/OR PRESSURE-SENSITIVE ADHESIVE FOR MEDICAL OR INDUSTRIAL USE, ADHESIVE SHEET AND/OR PRESSURE-SENSITIVE ADHESIVE SHEET FOR MEDICAL OR INDUSTRIAL USE, AND PRESSURE-SENSITIVE ADHESIVE TAPE FOR MEDICAL OR INDUSTRIAL USE

TECHNICAL FIELD

The present invention relates to a tackifier, a tackifier for medical or industrial use, an adhesive and/or pressure-sensitive adhesive for medical or industrial use, an adhesive sheet and/or pressure-sensitive adhesive sheet for medical or industrial use, and a pressure-sensitive adhesive tape for medical or industrial use. The term "adhesive and/or pressure-sensitive adhesive" herein refers to an adhesive as specified in JIS K 6800 and/or a pressure-sensitive adhesive as specified in JIS K 6800. The term "adhesive sheet and/or pressure-sensitive adhesive sheet" herein refers to an adhesive sheet and/or a pressure-sensitive adhesive sheet. The term "adhesive tape and/or pressure-sensitive adhesive tape" herein refers to an adhesive tape and/or a pressure-sensitive adhesive tape.

BACKGROUND ART

Compositions comprising an ester compound of a polyol and a resin acid such as abietic acid (hereinafter sometimes referred to as a resin acid ester) have been widely used as tackifiers to be blended in adhesives and/or pressure-sensitive adhesives for industrial use (see, for example, Patent Literature 1). In recent years, such compositions have also been favorably used as tackifiers for medical adhesive sheets and/or pressure-sensitive adhesive sheets (e.g., patches, cataplasms, wet compresses, etc.) or for medical tapes (e.g., adhesive bandages etc.) (see, for example, Patent Literature 2).

Such adhesives and/or pressure-sensitive adhesives comprise various high molecular weight copolymers as base resins. For example, synthetic rubber elastomers such as styrene-isoprene-styrene block copolymers (SISs) and styrene-butadiene-styrene block copolymers (SBSs) have an excellent elasticity and a good adhesion to substrates and are less harmful to the human body, and therefore the copolymers have been highly consumed in the commercial market of industrial adhesives and/or pressure-sensitive adhesives, especially in the commercial market of medical adhesives and/or pressure-sensitive adhesives.

Some adhesives and/or pressure-sensitive adhesives using synthetic rubber elastomers are provided as a varnish type with an organic solvent, and others are provided as a solvent-free hot melt type in consideration of the effects on the environment and human health. Needless to say, adhesive performance such as tack is required for both types, but the hot melt type has distinctive problems as described below.

That is, synthetic rubber elastomers are highly viscid even when heated and melted at a high temperature and thus it is often difficult to use them for coating with an applicator. Accordingly, the elastomers need to be melted at a much elevated temperature for the reduction of their viscosity. However, when synthetic rubber elastomers are heated at a very high temperature, effective ingredients such as a tackifying resin blended therein may deteriorate or decompose under the heat. Further, the substrate to which hot synthetic rubber elastomers are applied may be deformed by the heat. Moreover, a large amount of electricity is required for heating the elastomers at a very high temperature, which leads to increase in the final product cost.

CITATION LIST

Patent Literature

Patent Literature 1: JP 8-157789 A
Patent Literature 2: JP 2005-170833 A

SUMMARY OF INVENTION

Technical Problem

An object of the present invention is to provide a novel tackifier having a good compatibility with a synthetic rubber elastomer in a varnish state or hot melt state, being capable of effectively reducing the melt viscosity of the synthetic rubber elastomer in a hot melt state, and being capable of imparting excellent adhesive performance to the synthetic rubber elastomer.

Solution to Problem

The inventors have conducted extensive studies to solve the above problems and, as a result, have found that the problems can be solved by using a resin acid ester with specific parameters as a tackifier.

That is, the present invention relates to the following.
(1) A tackifier being composed of an ester composition, characterized by
(i) the ester composition comprising 70% by weight or more of a resin acid ester represented by the general formula (1):

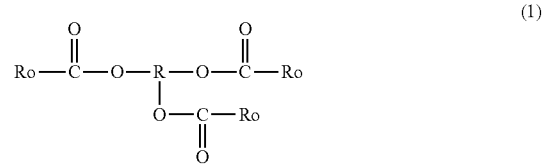

(wherein Ro represents a residue of a resin acid and R represents a residue of an aliphatic triol), and
(ii) the $S'_{NMR}/S_{NMR}$ ratio of the ester composition being at least 6% in the $^1$H-NMR spectrum of the ester composition, wherein $S'_{NMR}$ is the total integral value of the proton signal(s) appearing in the region of 6 to 8 ppm and $S_{NMR}$ is the total integral value of all the proton signals appearing over the entire range of the $^1$H-NMR spectrum.
(2) The tackifier according to the above (1), wherein the aliphatic triol is glycerin.
(3) The tackifier according to the above (1) or (2), which has a color tone of 200 Hazen units or less.
(4) The tackifier according to any of the above (1) to (3), wherein the ester composition has an acid value of 1 to 10 mg KOH/g and a hydroxyl value of 1 to 20 mg KOH/g.
(5) The tackifier according to any of the above (1) to (4), wherein the ester composition has a softening point of 90 to 110° C.
(6) The tackifier according to any of the above (1) to (5), which is for medical or industrial use.

(7) An adhesive and/or pressure-sensitive adhesive for medical or industrial use, the adhesive comprising the tackifier according to the above (6) and a synthetic rubber elastomer.
(8) The adhesive and/or pressure-sensitive adhesive according to the above (7), wherein the synthetic rubber elastomer is at least one type selected from the group consisting of styrene-isoprene-styrene block copolymers (SISs), styrene-butadiene-styrene block copolymers (SBSs), styrene-hydrogenated butadiene-styrene block copolymers (SEBSs) and styrene-ethylene/propylene-styrene copolymers (SEPSs).
(9) The adhesive and/or pressure-sensitive adhesive according to the above (7) or (8), wherein the amount of the tackifier is 50 to 200 parts by weight relative to 100 parts by weight of the synthetic rubber elastomer.
(10) An adhesive sheet and/or pressure-sensitive adhesive sheet for medical or industrial use obtainable using the adhesive and/or pressure-sensitive adhesive according to any of the above (7) to (9).
(11) An adhesive tape and/or pressure-sensitive adhesive tape for medical or industrial use obtainable using the adhesive and/or pressure-sensitive adhesive according to any of the above (7) to (9).

Advantageous Effects of Invention

The tackifier of the present invention is compatible with a synthetic rubber elastomer in a varnish state or hot melt state at low to high temperature. The tackifier is capable of effectively reducing the melt viscosity of a synthetic rubber elastomer in a hot melt state, thereby improving the coatability of the synthetic rubber elastomer. The blending of the tackifier of the present invention in a synthetic rubber elastomer can provide an adhesive composition and/or pressure-sensitive adhesive composition with excellent adhesive properties and/or pressure-sensitive adhesive properties such as tack, holding power and adhesive strength. The tackifier of the present invention is less discolored even under heating and can thus increase the product value of an adhesive composition and/or pressure-sensitive adhesive composition. That is, the present invention can provide a tackifier suitable for medical or industrial use, especially suitable for medical use.

The adhesive and/or pressure-sensitive adhesive of the present invention for medical use provides an adhesive layer and/or pressure-sensitive adhesive layer which has an adequate tack and an excellent adhesion to elastic or non-elastic substrates including synthetic resin sheets, synthetic resin films, sheet foams, woven fabrics, nonwoven fabrics, and the like. The adhesive and/or pressure-sensitive adhesive of the present invention for medical use can be used in the form of a varnish type or a hot melt type. Therefore, the adhesive and/or pressure-sensitive adhesive of the present invention for medical use can be effectively used as a material for, in particular, an adhesive sheet and/or pressure-sensitive adhesive sheet for medical use, such as patches, cataplasms and wet compresses, or an adhesive tape and/or pressure-sensitive adhesive tape for medical use, such as adhesive bandages.

The adhesive and/or pressure-sensitive adhesive of the present invention for industrial use is excellent in adhesive properties and/or pressure-sensitive adhesive properties, such as tack, holding power and adhesive strength. The adhesive and/or pressure-sensitive adhesive for industrial use can be used in the form of a varnish type or a hot melt type. Both types of the adhesive and/or pressure-sensitive adhesive are excellent in adhesion to paper substrates, plastic substrates or metal substrates. The adhesive and/or pressure-sensitive adhesive for industrial use can be used for various applications. In particular, the hot melt type adhesive and/or pressure-sensitive adhesive for industrial use can be effectively used as an adhesive for, for example, hygiene products such as paper diapers and sanitary napkins and automotive interior materials.

DESCRIPTION OF EMBODIMENTS

The present invention will be described in detail below.
The tackifier of the present invention is composed of an ester composition characterized by
(i) the ester composition comprising 70% by weight or more of a resin acid ester represented by the general formula (1):

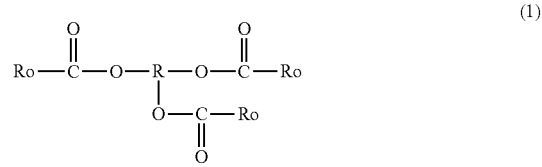

(wherein Ro represents a residue of a resin acid and R represents a residue of an aliphatic triol), and
(ii) the $S'_{NMR}/S_{NMR}$ ratio of the ester composition being at least 6% in the $^1$H-NMR spectrum of the ester composition, wherein $S'_{NMR}$ is the total integral value of the proton signal(s) appearing in the region of 6 to 8 ppm and $S_{NMR}$ is the total integral value of all the proton signals appearing over the entire range of the $^1$H-NMR spectrum.

The ester composition comprises a resin acid ester represented by the general formula (1) in an amount of usually 70% by weight or more, preferably about 80 to 90% by weight. If the amount of the resin acid ester is less than 70% by weight, the tackifying performance of the ester composition becomes insufficient.

In the present invention, the amount (% by weight) of the resin acid ester contained in the ester composition can be determined by various known methods. Usually, the amount is determined by performing gel permeation chromatography (GPC) on the ester composition, and then calculating the ratio represented by $S'_{GPC}/S_{GPC}$, wherein $S'_{GPC}$ is the area of the peak (s) corresponding to the resin acid ester and $S_{GPC}$ is the total area of all the peaks in the GPC chromatograph. The details of the conditions of GPC measurement for the amount of the resin acid ester contained in the ester composition of the present invention will be illustrated in Examples described later.

The "residue of a resin acid" represented by Ro in said formula (1) is a chemical structure corresponding to a resin acid's structure from which the tertiary carboxyl group is eliminated.

Specific examples of the resin acid include abietic acid, palustric acid, neoabietic acid, pimaric acid, isopimaric acid, dehydroabietic acid, tetrahydroabietic acid, dihydroabietic acid, and the like, but are not particularly limited thereto. Among these, preferred is at least one selected from the group consisting of dehydroabietic acid, tetrahydroabietic acid, and dihydroabietic acid because of their excellent heat stability.

The "residue of an aliphatic triol" represented by R in said formula (1) is a chemical structure corresponding to an aliphatic trial's structure from which all the hydroxy groups are eliminated. Specific examples of the aliphatic triol include glycerin, trimethylolethane, trimethylolpropane, and the like, but are not particularly limited thereto. Among these, preferred is glycerin because use of glycerin can achieve much higher adhesive performance or pressure-sensitive adhesive performance of the adhesive and/or pressure-sensitive adhesive. If the aliphatic triol is replaced with, for example, an aliphatic diol or an aliphatic tetraol, the resulting ester composition tends to be insufficient in its tackifying performance, tends to fail to exhibit sufficient reduction effect on the melt viscosity of the synthetic rubber elastomer, or tends to be strongly colored.

In the $^1$H-NMR spectrum of the ester composition, the $S'_{NMR}/S_{NMR}$ ratio, wherein $S'_{NMR}$ is the total integral value of the proton signal(s) appearing in the region of 6 to 8 ppm and $S_{NMR}$ is the total integral value of all the proton signals appearing over the entire range of the $^1$H-NMR spectrum, is at least 6%, preferably 6% to 10%. If the ratio is less than 6%, the ester composition cannot exhibit sufficient reduction effect on the melt viscosity of the synthetic rubber elastomer.

The $S'_{NMR}/S_{NMR}$ ratio herein indicates the amount of aromatic ring moieties present in the ester composition.

The "region of 6 to 8 ppm" herein is the $^1$H-NMR spectral region wherein a (signal) peak(s) attributed to the aromatic ring(s) appear(s), which aromatic ring(s) constitute(s) an aromatic-ring-containing compound contained in the ester composition. Therefore, when a peak is considered to be attributed to an aromatic ring, the peak may be taken as a peak appearing in the "region of 6 to 8 ppm". Examples of the aromatic-ring-containing compound include ester compounds (including monoesters, diesters and triesters) of dehydroabietic acid (see the chemical formula (2) below) and an aliphatic triol; free dehydroabietic acid; etc. From the above-mentioned peaks appearing in the "region of 6 to 8 ppm", the peak attributed to a NMR measurement solvent (deuterated chloroform etc.) has been removed. The above-mentioned "total integral value of all the proton signals ($S_{NMR}$)" is the total integral value of all the proton signals from which the integral value of the peak attributed to a NMR measurement solvent is subtracted.

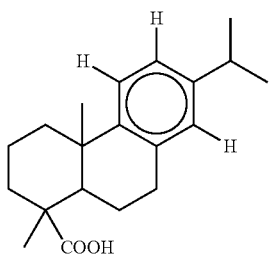

(2)

The method for producing the ester composition of the present invention is not particularly limited and various conventional methods in the art can be employed. Specifically, such methods are illustrated by the following methods.

[1] A synthetic method in which any type of resin acid and any type of aliphatic triol are esterified into a resin acid ester represented by the general formula (1)

In this method, when the amount of the resin acid ester in the resulting composition is 70% by weight or more, a purification step of the resin acid ester is not required.

[2] A method in which the resin acid ester obtained by the above method [1] is mixed with any type of molten rosin so that the final resin acid ester content becomes 70% by weight or more The rosin herein is a resin component that may comprise, in addition to the above resin acid, another component including an essential oil such as a turpentine oil.

[3] A method in which any type of rosin and any type of aliphatic triol are reacted to provide a composition and, in cases where the amount of a resin acid ester represented by the general formula (1) in the resulting composition is less than 70% by weight, the composition is purified by various known methods, that is, the reaction composition is purified so that the resulting ester composition comprises 70% by weight or more of a resin acid ester represented by the general formula (1)

The resin acid used in the above method [1] is not particularly limited and the resin acid may be, for example, a highly purified resin acid obtainable from a raw material rosin through various known treatments such as hydrotreatment, heat treatment, purification treatment, and the like. The resin acid may also be a commercially available product. Examples of the raw material rosin include gum rosin, wood rosin, tall oil rosin, and the like. The rosin may be any one of these or a combination of two or more of these.

In the above method [1], the conditions for the reaction of the resin acid and the aliphatic triol are not particularly limited as long as the resin acid ester content is to be 70% by weight or more. For example, the reaction temperature may be usually about 150° C. to 300° C. The amounts of the resin acid and the aliphatic triol are not particularly limited and may be in any ratio, but usually the reaction molar ratio of the resin acid to the aliphatic triol is about 1:2 to about 2:1.

In the above method [2], the rosin is not particularly limited and examples thereof include the above-described raw material rosin, a hydrogenated rosin, a disproportionated rosin, a polymerized rosin, a purified rosin, and the like. The rosin may be any one of these or a combination of two or more of these.

In the above method [3], the conditions for the reaction of the rosin and the triol are not particularly limited. For example, the reaction temperature may be usually about 150° C. to 300° C. The amounts of the resin acid and the aliphatic triol are not particularly limited but need to be determined in consideration of the amount of the resin acid ester represented by the general formula (1) to be contained in the ester composition (in particular, 70% by weight or more). The amount of the triol is usually about 5 to 20 parts by weight relative to 100 parts by weight of the rosin. The resulting composition may be subjected to various known treatments such as hydrotreatment, heat treatment, purification treatment, and the like.

The ester composition of the present invention may comprise a component other than the resin acid ester represented by the above general formula (1). Examples of the component include a reaction product of one or two molecules of a resin acid and one molecule of an aliphatic triol (i.e., a monoester and/or a diester), an unreacted resin acid and an unreacted aliphatic triol, a low boiling point component with a molecular weight of 300 or less (e.g., a catalyst used in the esterification reaction, a solvent component, an essential oil contained in the rosin, or the like), etc. The total amount of the components other than the resin acid ester represented by the above general formula (1) is usually less than 30% by weight, preferably about 10 to 20% by weight.

The characteristics of the ester composition of the present invention are not particularly limited but, for example, the ester composition usually has a color tone of 200 Hazen units or less, preferably 10 to 150 Hazen units. The tackifier being composed of the ester composition with such a color tone hardly deteriorate or decompose under heating, and consequently an adhesive and/or pressure-sensitive adhesive using the tackifier will have an adequate color tone, a good heat resistance and other benefits. The term "Hazen unit" refers to a value of color tone on the Hazen scale measured in accordance with the method described in JIS K 0071: 1998.

In a preferred embodiment, the acid value (see JIS K 5902) of the ester composition of the present invention is usually about 1 to 10 mg KOH/g, preferably 3 to 8 mg KOH/g, and the hydroxyl value (see JIS K 0070) of the ester composition is usually about 1 to 20 mg KOH/g, preferably 5 to 15 mg KOH/g. The ester composition having such an acid value and a hydroxyl value imparts particularly excellent adhesive performance or pressure-sensitive adhesive performance to an adhesive and/or pressure-sensitive adhesive.

In a preferred embodiment, the softening point (see JIS K 5902) of the ester composition of the present invention is usually about 90 to 110° C., preferably 90 to 105° C. The ester composition having such a softening point imparts particularly excellent adhesive performance or pressure-sensitive adhesive performance to an adhesive and/or pressure-sensitive adhesive.

The tackifier of the present invention illustrated above is useful as a tackifier for medical or industrial use.

In one embodiment of the present invention, the tackifier is suitable for an adhesive and/or pressure-sensitive adhesive for medical or industrial use. The adhesive and/or pressure-sensitive adhesive for medical or industrial use comprises the tackifier of the present invention and a synthetic rubber elastomer. The synthetic rubber elastomer is not particularly limited and examples thereof include styrene-isoprene-styrene block copolymers (SISs), styrene-butadiene-styrene block copolymers (SBSs), styrene-hydrogenated butadiene-styrene block copolymers (SEBSs), styrene-ethylene/propylene-styrene copolymers (SEPSs), etc. The synthetic rubber elastomer may be any one of these or a combination of two or more of these. Among these, particularly preferred are SISs and/or SBSs in view of achieving better adhesive performance or pressure-sensitive adhesive performance.

In another embodiment of the present invention, the amounts of the tackifier and the synthetic rubber elastomer are not particularly limited, but in view of achieving balanced adhesive performance and/or pressure-sensitive adhesive performance of the adhesive and/or pressure-sensitive adhesive of the present invention, the amount of the tackifier is usually about 50 to 200 parts by weight, preferably 100 to 200 parts by weight, relative to 100 parts by weight of the synthetic rubber elastomer.

If necessary, the adhesive and/or pressure-sensitive adhesive of the present invention may comprise another tackifier. Specific examples of the tackifier include rosin-based tackifying resins such as the above-described raw material rosin, a purified rosin, a hydrogenated rosin, a disproportionated rosin, and a polymerized rosin (not including an equivalent to the ester composition of the present invention); non-rosin based-tackifying resins such as a coumarone-indene resin, a phenol-formaldehyde resin, a modified xylene resin, a terpene-phenol resin, a hydrogenated terpene resin, and a hydrogenated petroleum resin; etc. The tackifier may be any one of these or a combination of two or more of these. The amount of the tackifier is not particularly limited but is usually about 0 to 200 parts by weight relative to 100 parts by weight of the synthetic rubber elastomer.

The synthetic rubber elastomer for forming the adhesive and/or pressure-sensitive adhesive of the present invention may be used together with various known base resins. The known base resins are not particularly limited and specific examples thereof include an acrylic copolymer, a natural latex, a polyurethane resin, a liquid polybutadiene, a liquid polyisobutylene, a gelatin, a mannan, a starch, etc. The base resins can be appropriately selected depending on whether the adhesive and/or pressure-sensitive adhesive is for industrial use or medical use. The amounts of the base resins are not particularly limited but are usually about 0 to 100 parts by weight relative to 100 parts by weight of the synthetic rubber elastomer.

If necessary, the adhesive and/or pressure-sensitive adhesive of the present invention can comprise various types of additives. The additives are not particularly limited and specific examples thereof include inorganic fillers such as calcium carbonate, flowers of zinc, talc, silica, and magnesium carbonate; an antioxidant; an ultraviolet absorber; a thixotropic agent; paraffin oil; etc. In particular cases where the adhesive and/or pressure-sensitive adhesive of the present invention is used to produce the after-mentioned medical sheet or medical tape, the adhesive and/or pressure-sensitive adhesive can comprise, as an additive, various types of drugs, an antibacterial agent, an antihistamine, a cooling agent, a fragrance, a water absorbing component, a softening agent, or the like. The amount of such an additive is not particularly limited but is usually about 0 to 10 parts by weight relative to 100 parts by weight of the synthetic rubber elastomer. However, paraffin oil can be used usually in an amount of about 100 to 150 parts by weight relative to 100 parts by weight of the synthetic rubber elastomer.

The adhesive and/or pressure-sensitive adhesive of the present invention can be used in the form of a varnish type or a hot melt type.

The varnish type adhesive and/or pressure-sensitive adhesive can comprise various types of organic solvents. The organic solvents are not particularly limited and specific examples thereof include toluene, xylene, methyl ethyl ketone, acetone, ethyl acetate, cyclohexane, methylcyclohexane, methanol, ethanol, propanol, hexylene glycol, etc. The organic solvents can be appropriately selected depending on whether the adhesive and/or pressure-sensitive adhesive is for industrial use or medical use. The amounts of the organic solvents are not particularly limited but are usually about 100 to 500 parts by weight, preferably 200 to 300 parts by weight, relative to 100 parts by weight of the synthetic rubber elastomer.

However, the hot-melt type adhesive and/or pressure-sensitive adhesive does not require organic solvents, which are used for the above varnish type adhesive and/or pressure-sensitive adhesive. The melt viscosity of the hot melt type adhesive and/or pressure-sensitive adhesive of the present invention is not particularly limited but the melt viscosity at 200° C. is usually about 1,000 to 100,000 mPa·s, preferably 1,000 to 20,000 mPa·s. The viscosity is measured with a B-type viscometer (product name: VISCO BLOCK VTB-250 (TOKIMEC CO., LTD.), rotor No.: HM-3).

Another embodiment of the present invention relates to an adhesive sheet and/or pressure-sensitive adhesive sheet for medical or industrial use obtained using the above adhesive and/or pressure-sensitive adhesive.

Another embodiment of the present invention relates to an adhesive tape and/or pressure-sensitive adhesive tape for medical or industrial use obtained using the above adhesive and/or pressure-sensitive adhesive.

The adhesive sheet and/or pressure-sensitive adhesive sheet of the present invention for medical or industrial use and the adhesive tape and/or pressure-sensitive adhesive tape of the present invention for medical or industrial use may be produced by coating any type of substrate with the adhesive and/or pressure-sensitive adhesive of the present invention. The substrate is not particularly limited and examples thereof include papers, plastics, metals, woods, etc. The shape of the substrate is not particularly limited but the shape is usually in a form of a sheet or tape and may be in a form of a round bar, a square bar, a woven fabric, or a nonwoven fabric. The plastics are not particularly limited and examples thereof include cellophane, polyethylene, polystyrene, polypropylene, polyester, etc.

In one embodiment of the present invention, a woven or nonwoven fabric with elasticity is suitable as the substrate of the above medical sheet or tape.

In the production of the above medical or industrial sheet or the above medical or industrial tape, the method for coating the above substrate with the adhesive and/or pressure-sensitive adhesive of the present invention is not particularly limited and various conventional methods in the art may be employed. Specific examples of such methods include a method in which the adhesive and/or pressure-sensitive adhesive is directly applied to, spread on, or applied as a coating on the surface of a substrate; a method in which the adhesive and/or pressure-sensitive adhesive is first applied as a coating on a substrate having a release liner by means of an applicator and then transferred to a desired substrate; and the like. The thicknesses of the above substrate and of the above adhesive layer or pressure-sensitive adhesive layer are not particularly limited and appropriately selected depending on the type of product for which the adhesive and/or pressure-sensitive adhesive of the present invention is used.

EXAMPLES

The present invention will be described in more detail below with reference to experimental examples and Examples, but the present invention is not limited thereto. Various modifications are possible within the technical idea of the present invention by a person who has ordinary knowledge in the art.

The quantitative analysis of the resin acid esters in Production Examples below was conducted using a commercially available gas chromatography device (product name: GC-14A (Shimadzu Corporation)). The column was a commercially available product (trade name: Advance-DS (Shinwa Chemical Industries Ltd.)).

Production Example 1

Production of Dehydroabietic Acid

A commercially available disproportionated rosin (acid value: 167 mg KOH/g, softening point: 77° C. (Arakawa Chemical Industries, Ltd.)) was melt in argon flow and heated under reduced pressure of 1.3 kPa to provide a fraction at 195 to 200° C. and 0.47 kPa. This fraction had an acid value of 180 mg KOH/g and a softening point of 93° C.

In 480 g of ethanol was dissolved 200 g of the fraction under heating, and 40 g of monoethanolamine was added. The mixture was reacted under reflux for 1 hour. To the mixture, 500 g of water was added to prepare an aqueous solution of a monoethanolamine salt of dehydroabietic acid.

To this aqueous solution, 200 mL of isooctane was added, and unsaponifiable matter and dihydroabietic acid salts were transferred to the isooctane layer, thereby extracting the monoethanolamine salt of dehydroabietic acid. This procedure was repeated once more. The aqueous layer was transferred to a container and left to stand overnight. The precipitated crystals were filtered. Ethanol recrystallization of the crystals was performed three times to increase the purity and hydrochloric acid was added to provide dehydroabietic acid crystals.

The obtained crystals were collected by filtration. The crystals were dissolved in ether and sufficiently washed with water, and the ether was evaporated under reduced pressure so that the crystals were sufficiently dried. The resultant dried crystals were recrystallized again in ethanol and filtered to provide highly purified dehydroabietic acid crystals of interest. The thus obtained crystals of dehydroabietic acid had an acid value of 186 mg KOH/g and a melting point of 178° C.

In 2.0 g of n-hexanol was dissolved 0.1 g of the crystals of dehydroabietic acid, and 0.1 g of the resultant solution was uniformly mixed with 0.4 g of an on-column methylation reagent (trade name: Phenyltrimethylammonium Hydroxide (PTAH) 0.2 mol Solution in Methanol (GL Sciences Inc.)). Then, 1 μL of the mixture was injected into the above-described gas chromatography device to perform composition analysis and quantitative analysis. The analysis revealed that the purity of dehydroabietic acid was 96%.

Production Example 2

Production of Tetrahydroabietic Acid

A commercially available abietic acid in an amount of 300 g (melting point: 172 to 175° C. (Kanto Chemical Co., Ltd.)) was placed in an autoclave together with 500 g of cyclohexane and 15 g of a nickel-diatomaceous earth catalyst (trade name: N-113 (JGC Chemicals Ltd.)). The atmosphere was replaced with hydrogen and the pressure in the container was raised to 10 MPa to perform hydrogenation reaction at 250° C. for 5 hours. The reaction container was allowed to cool down to room temperature. The solution in the container was blown with hydrogen and the catalyst was removed by filtration under nitrogen atmosphere to provide a solution of crude tetrahydroabietic acid in cyclohexane. The resultant solution was subjected to recrystallization twice in acetone. The recrystallized crystals were collected by filtration and sufficiently dried under reduced pressure. The thus obtained crystals of tetrahydroabietic acid had an acid value of 194, a melting point of 170° C. and a gas chromatographic purity of 97%.

Production Example 3

Production of Dihydroabietic Acid

An unpurified gum rosin made in China in an amount of 100 g was placed in an autoclave together with 100 g of mineral turpentine and 5 g of a Raney nickel catalyst. The atmosphere was replaced with hydrogen and the pressure in the container was raised to 10 MPa to perform hydrogenation reaction at 110° C. for 5 hours. The reaction container was allowed to cool down to room temperature. The solution in the container was blown with hydrogen and the catalyst was removed by filtration under nitrogen atmosphere to provide a solution of dihydroabietic acid in mineral turpentine. To 100 g of the resultant solution, 0.2 g of p-toluenesulfonic acid was added to perform isomerization at 150° C. for 2 hours. Mineral turpentine and p-toluenesulfonic acid were removed by vacuum distillation to provide crude crystals of dihydroabietic acid. The crude crystals were subjected to recrystallization in acetone four times. The recrystallized crystals were collected by filtration and sufficiently dried under reduced pressure. The thus obtained crystals of dihydroabietic acid had an acid value of 194, a melting point of 182° C. and a gas chromatographic purity of 98%.

Example 1

Into a four-necked flask were placed 69 g of dehydroabietic acid obtained in Production Example 1, 11 g of tetrahydroabietic acid obtained in Production Example 2 and 20 g of dihydroabietic acid obtained in Production Example 3. The flask was blanketed with argon and the mixture was heated at 180° C. While the molten mixture was stirred, 12 g of glycerin was added at 200° C. and esterification reaction was performed at 280° C. for 12 hours to provide 103 g of a resin acid ester composition (A1). The water generated by the esterification was discharged to the outside of the system via a partial condenser. In this example, a SIS (styrene-isoprene-styrene block copolymer) was used for the evaluation of the composition's performance for adhesives. The characteristics are shown in Table 1.

Calculation of $S'_{GPC}/S_{GPC}$ Ratio

The ester composition was dissolved in tetrahydrofuran to prepare a 0.5% (w/v) solution. This solution was analyzed on a commercially available gel permeation chromatography device (product name: HLC-8120 (TOSOH CORPORATION); column: TSK-GEL SUPER HM-L (TOSOH CORPORATION), three columns connected in series; detector: RI; measurement temperature: 40° C.; liquid flow rate: 0.6 mL/min) to produce a chromatogram. The $S'_{GPC}/S_{GPC}$ ratio was calculated by the mathematical formula (i) below to be 85%. From this value, the amount of the resin acid ester of the general formula (1) in the ester composition was determined to be 83% by weight.

Mathematical formula (i):

$S'_{GPC}/S_{GPC}$ ratio(%)=[area of peak(s) corresponding to weight average molecular weight of 800(in terms of polystyrene)($S'_{GPC}$)/total area of all peaks($S_{GPC}$)]×100

Calculation of $S'_{NMR}/S_{NMR}$ Ratio

The above ester composition was dissolved in a deuterated chloroform solvent to prepare a 5% (w/v) solution. This solution was analyzed on a commercially available $^1$H-NMR spectrometer (product name: GEMINI-300 (300 MHz) (Varian Inc.)) to produce a spectrum. The $S'_{NMR}/S_{NMR}$ ratio was calculated by the mathematical formula (ii) below to be 8%. From this value, the total amount of the aromatic ring moieties in the ester composition was determined.

Mathematical formula (ii):

$S'_{NMR}/S_{NMR}$ ratio(%)=[total integral value of the proton signal(s) appearing in the region of 6 to 8 ppm($S'_{NMR}$)/total integral value of all the proton signals appearing over the entire range($S_{NMR}$)]×100

Example 2

A resin acid ester composition (A2) was prepared in an amount of 101 g in the same manner as in Example 1 except that the amount of dehydroabietic acid was 57 g, that the amount of tetrahydroabietic acid was 25 g, and that the amount of dihydroabietic acid was 18 g. In this example, a SIS was used for the evaluation of the composition's performance for adhesives. The characteristics are shown in Table 1.

Example 3

A resin acid ester composition (A3) was prepared in an amount of 103 g in the same manner as in Example 1 except that the amount of dehydroabietic acid was 79 g, that the amount of tetrahydroabietic acid was 11 g, and that the amount of dihydroabietic acid was 10 g. In this example, a SIS was used for the evaluation of the composition's performance for adhesives. The characteristics are shown in Table 1.

Example 4

Into a four-necked flask were placed 61 g of dehydroabietic acid obtained in Production Example 1, 20 g of tetrahydroabietic acid obtained in Production Example 2 and 19 g of dihydroabietic acid obtained in Production Example 3. The flask was blanketed with argon and the mixture was heated at 180° C. While the molten mixture was stirred, 18 g of trimethylolpropane was added at 200° C. and esterification reaction was performed at 280° C. for 12 hours to provide 109 g of a resin acid ester composition (A4). In this example, a SIS was used for the evaluation of the composition's performance for adhesives. The characteristics are shown in Table 1.

Example 5

A resin acid ester composition was prepared in the same manner as in Example 1 but a SBS (styrene-butadiene-styrene block copolymer) was used for the evaluation of the composition's performance for adhesives. The characteristics are shown in Table 1.

Example 6

A resin acid ester composition was prepared in the same manner as in Example 2 but a SBS was used for the evaluation of the composition's performance for adhesives. The characteristics are shown in Table 1.

Example 7

A resin acid ester composition was prepared in the same manner as in Example 3 but a SBS was used for the evaluation of the composition's performance for adhesives. The characteristics are shown in Table 1.

Example 8

A resin acid ester composition was prepared in the same manner as in Example 4 but a SBS was used for the evaluation of the composition's performance for adhesives. The characteristics are shown in Table 1.

Comparative Example 1

A resin acid ester composition (B1) was prepared in an amount of 102 g in the same manner as in Example 1 except that the amount of dehydroabietic acid was 45 g, that the amount of tetrahydroabietic acid was 30 g, and that the amount of dihydroabietic acid was 25 g. In this example, a SIS was used for the evaluation of the composition's performance for adhesives. The characteristics are shown in Table 2.

Comparative Example 2

A resin acid ester composition (B2) was prepared in an amount of 102 g in the same manner as in Example 1 except that the amount of dehydroabietic acid was 31 g, that the amount of tetrahydroabietic acid was 62 g, and that the amount of dihydroabietic acid was 7 g. In this example, a SIS was used for the evaluation of the composition's performance for adhesives. The characteristics are shown in Table 2.

Comparative Example 3

A resin acid ester composition (B3) was prepared in an amount of 102 g in the same manner as in Example 1 except that the amount of dehydroabietic acid was 65 g, that the amount of tetrahydroabietic acid was 17 g, and that the amount of dihydroabietic acid was 18 g. In this example, a SIS was used for the evaluation of the composition's performance for adhesives. The characteristics are shown in Table 2.

Comparative Example 4

A resin acid ester composition (B4) was prepared in an amount of 102 g in the same manner as in Example 1 except that the amount of dehydroabietic acid was 35 g, that the amount of tetrahydroabietic acid was 60 g, and that the amount of dihydroabietic acid was 5 g. In this example, a SIS was used for the evaluation of the composition's performance for adhesives. The characteristics are shown in Table 2.

Comparative Example 5

A commercially available gum rosin made in China (acid value: 170, softening point: 77° C. (Arakawa Chemical Industries, Ltd.)) was blanketed with nitrogen and distilled under a reduced pressure of 3 mmHg to provide a purified rosin with an acid value of 175, a softening point of 79° C. and a color tone of 250 Hazen units. The purified rosin was esterified with glycerin in the same manner as in Example 1 to provide 103 g of a resin acid ester composition. The ester composition in an amount of 100 g was placed in an autoclave together with 100 g of cyclohexane and 3.0 g of a 5% Pd-carbon catalyst (with 50% water (N.E. Chemcat Corporation)). The atmosphere in the reaction container was replaced with hydrogen and the pressure was raised to 15 MPa to perform hydrogenation reaction at 290° C. for 4 hours. After the end of the reaction, the reaction container was allowed to cool down. The solution was blown with hydrogen and the catalyst was removed by filtration to provide a solution of an ester composition in cyclohexane. Cyclohexane was removed by vacuum distillation from the solution to provide 96 g of a resin acid ester composition (B5). In this example, a SIS was used for the evaluation of the composition's performance for adhesives. The characteristics are shown in Table 2.

Comparative Example 6

A resin acid ester composition (B6) was prepared in an amount of 112 g in the same manner as in Example 1 except that 21 g of diethylene glycol was used instead of 12 g of glycerin. In this example, a SIS was used for the evaluation of the composition's performance for adhesives. The characteristics are shown in Table 2.

Comparative Example 7

A resin acid ester composition (B7) was prepared in an amount of 105 g in the same manner as in Example 1 except that 14 g of pentaerythritol was used instead of 12 g of glycerin. In this example, a SIS was used for the evaluation of the composition's performance for adhesives. The characteristics are shown in Table 2.

Comparative Example 8

A resin acid ester composition was prepared in the same manner as in Comparative Example 1 but a SBS was used for the evaluation of the composition's performance for adhesives. The characteristics are shown in Table 3.

Comparative Example 9

A resin acid ester composition was prepared in the same manner as in Comparative Example 2 but a SBS was used for the evaluation of the composition's performance for adhesives. The characteristics are shown in Table 3.

Comparative Example 10

A resin acid ester composition was prepared in the same manner as in Comparative Example 3 but a SBS was used for the evaluation of the composition's performance for adhesives. The characteristics are shown in Table 3.

Comparative Example 11

A resin acid ester composition was prepared in the same manner as in Comparative Example 4 but a SBS was used for the evaluation of the composition's performance for adhesives. The characteristics are shown in Table 3.

Comparative Example 12

A resin acid ester composition was prepared in the same manner as in Comparative Example 5 but a SBS was used for the evaluation of the composition's performance for adhesives. The characteristics are shown in Table 3.

Comparative Example 13

A resin acid ester composition was prepared in the same manner as in Comparative Example 6 but a SBS was used for the evaluation of the composition's performance for adhesives. The characteristics are shown in Table 3.

Comparative Example 14

A resin acid ester composition was prepared in the same manner as in Comparative Example 7 but a SBS was used for the evaluation of the composition's performance for adhesives. The characteristics are shown in Table 3.

Performance Evaluation of Resin Acid Ester Compositions as Tackifiers

Measurement of Melt Viscosity of Hot Melt Type SIS-Based Pressure-Sensitive Adhesives The ester composition (A1) of Example 1 in an amount of 4 g was mixed with 4 g of a SIS (trade name: Quintac 3421 (ZEON CORPORATION)) and 1.2 g of paraffin oil (trade name: DI Process PW 90 (Idemitsu Kosan Co., Ltd.)). The mixture was heated stepwise from 120° C. to 140° C., 160°

C., 180° C. and 200° C. and the melt viscosity (mPa·s) was measured at each temperature step with a B-type viscometer (product name: VISCO BLOCK VTB-250, rotor No.: HM-3 (TOKIMEC CO., LTD.)). In the same manner as above, the melt viscosity of the resin acid ester compositions of Examples 2 to 4 and Comparative Examples 1 to 7 was measured at each temperature step. The melt viscosity is an indicator for coatability, that is, an ester composition that shows a lower melt viscosity at low temperature exhibits a higher reduction effect on the melt viscosity of a SIS and thereby improving the coatability of the SIS. Tables 1 to 3 show the evaluation results of the coatability based on the following criteria.

Good (A): viscosity of less than 200,000 mPa·s at 120° C. or 140° C.

Poor (C): viscosity of 200,000 or more at 120° C. or 140° C., or too high viscosity to be measured Evaluation of Pressure-Sensitive Adhesive Properties of Hot Melt Type SIS-Based Pressure-Sensitive Adhesives The ester composition of Example 1 in an amount of 4 g was mixed with 4 g of Quintac 3421 and 1.2 g of DI Process PW 90. The mixture was heated and melted at 200° C. and applied to an aluminum foil by hot melt coating (coating width: 25 mm) with a bar coater (No. 24) so that the thickness of the coating was about 60 μm, and thus a sample tape was prepared. In the same manner as above, sample tapes were prepared using the resin acid ester compositions of Examples 2 to 4 and Comparative Examples 1 to 7.

Adhesive Strength

The test was performed in accordance with JIS Z 0237. The sample tape prepared using the composition of Example 1 was attached to a polyethylene plate and pressed with a 2-kg rubber coated roller so that the adhesive contact area was 25 mm×125 mm. The substrate to which the tape was attached was left to stand at 20° C. for 24 hours. The substrate was then set on a Tensilon tension tester (product name: RMT-500 (ORIENTEC Co., Ltd.)) and 180° peel test (testing room temperature: 20° C., peel rate: 300 mm/min) was performed to measure an adhesive strength per unit width (N/25 mm). In the same manner as above, the adhesive strength was measured for the sample tapes prepared using the compositions of Examples 2 to 4 and Comparative Examples 1 to 7. A higher value means a higher adhesive strength.

Holding Power

The test was performed in accordance with the PSTC-7 method (the standard test method for holding power developed by The Pressure Sensitive Tape Council (the United States)). The sample tape prepared using the composition of Example 1 was attached to a stainless steel plate and pressed with a 2-kg rubber coated roller so that the adhesive contact area was 25 mm×25 mm. The substrate to which the tape was attached was left to stand at 20° C. for 24 hours. The substrate was then set on a creep tester (product name: Holding Power Tester (TESTER SANGYO CO., LTD.)) and 1 kg of load was applied at 40° C. for 3 hours. The amount of the slippage (mm) of the sample tape (the adhesive surface) on the stainless steel plate was measured. In the same manner as above, the holding power was measured for the sample tapes prepared using the compositions of Examples 2 to 4 and Comparative Examples 1 to 7. A smaller value means a higher holding power.

Ball Tack

The test was performed in accordance with the PSTC-6 method (the standard test method for holding power developed by The Pressure Sensitive Tape Council (the United States)). A steel ball (No. 14) was released from the top of a 30 degree inclined slope of a test stand to allow the ball to roll to a stop on the pressure-sensitive adhesive surface of the sample tape of Example 1 that was aligned with the slope. The distance (cm) where the ball rolled on the adhesive surface was measured. In the same manner as above, the ball tack was measured for the sample tapes prepared using the compositions of Examples 2 to 4 and Comparative Examples 1 to 7. A smaller value means a higher ball tack. The ball tack test is a method for evaluating the ability of a sample tape to adhere quickly to another surface.

Probe Tack

The sample tape prepared using the composition of Example 1 was set on NS Probe Tack Tester (Nichiban Co., Ltd.) and the probe tack (N/25 mm ϕ) was measured with a load of 100 g/cm² at a dwell time of 1 second. In the same manner as above, the probe tack was measured for the sample tapes prepared using the compositions of Examples 2 to 4 and Comparative Examples 1 to 7. A higher value means a higher probe tack. The probe tack test is a method for evaluating the force required to vertically separate a probe from a sample tape.

Comprehensive Evaluation

The comprehensive evaluation of the ester compositions when used for hot melt type pressure-sensitive adhesives were carried out based on the following criteria, using the measured values of the adhesive strength, holding power, ball tack and probe tack.

Good (A): adhesive strength of 25.0 or more, holding power of less than 5.0, ball tack of less than 4.0, and probe tack of 6.0 or more Fair (B): adhesive strength of less than 25.0, holding power of 5.0 or more, ball tack of 4.0 or more, or probe tack of less than 6.0

Measurement of Melt Viscosity of Hot Melt Type SBS-Based Pressure-Sensitive Adhesives The ester composition (A1) of Example 5 in an amount of 3.4 g was mixed with 3.4 g of a SBS (trade name: Kraton D1102 JSZ (Kraton Performance Polymers Inc.)) and 2 g of naphthenic oil (trade name: JCT OIL B (Japan Chemtech Ltd.)), and the mixture was heated stepwise from 120° C. to 140° C., 160° C., 180° C. and 200° C. The melt viscosity (mPa·s) was measured at each temperature step with a B-type viscometer (rotor No.: HM-3 (TOKYO KEIKI INC.)). In the same manner as above, the melt viscosity of the resin acid ester compositions of Examples 6 to 8 and Comparative Examples 8 to 14 was measured at each temperature step. Tables 1 to 3 show the evaluation results of the coatability based on the following criteria.

Good (A): viscosity of less than 200,000 mPa·s at 120° C. or 140° C.

Poor (C): viscosity of 200,000 or more at 120° C. or 140° C., or too high viscosity to be measured Evaluation of Pressure-Sensitive Adhesive Properties of Hot Melt Type SBS-Based Pressure-Sensitive Adhesives The ester composition (A1) of Example 5 in an amount of 3.4 g was mixed with 3.4 g of Kraton D1102 JSZ and 2 g of JCT OIL B. The mixture was heated and melted at 200° C. and applied to an aluminum foil by hot melt coating (coating width: 25 mm) with a bar coater (No. 14) so that the thickness of the coating was about 30 μm, and thus a sample tape was prepared. In the same manner as above, sample tapes were prepared using the resin acid ester compositions of Examples 6 to 8 and Comparative Examples 8 to 14. The adhesive strength, holding power, ball tack and probe tack of the tapes were measured and the comprehensive evaluation of the ester compositions when used for pressure-sensitive adhesives was carried out in the same manner as in the evaluation of pressure-sensitive adhesive properties of hot melt type SIS-based pressure-sensitive adhesives.

Evaluation of Pressure-Sensitive Adhesive Properties of Varnish Type SIS-Based Pressure-Sensitive Adhesives In 115 g of toluene were dissolved 50 g of the ester composition (A1) of Example 1, 50 g of Quintac 3421 and 15 g of DI Process PW 90 to prepare a varnish. A 38-μm thick polyester film was coated with the varnish with a cube applicator so that the dry thickness of the coating was about 30 μm (coating width: 25 mm). The coated film was dried with an air circulation dryer at 105° C. for 5 minutes to provide a sample tape. In the same manner as above, sample tapes were prepared using the resin acid ester compositions of Examples 2 to 4 and Comparative Examples 1 to 7. The adhesive strength, holding power and ball tack were measured in the same manner as in the evaluation of pressure-sensitive adhesive properties of hot melt type SIS-based pressure-sensitive adhesives.

Comprehensive Evaluation

The comprehensive evaluation of the ester compositions when used for varnish type pressure-sensitive adhesives were carried out based on the following criteria, using the measured values of the adhesive strength, holding power and ball tack.

Good (A): adhesive strength of 13.0 or more, holding power of less than 0.4 and ball tack of less than 11.0

Fair (B): adhesive strength of less than 13.0, holding power of 0.4 or more or ball tack of 11.0 or more Evaluation of Pressure-Sensitive Adhesive Properties of Varnish Type SBS-Based Pressure-Sensitive Adhesives In 110 g of toluene were dissolved 42.5 g of the ester composition (A1) of Example 5, 42.5 g of Kraton D1102 JSZ and 25 g of JCT OIL B to prepare a varnish. A 38-μm thick polyester film was coated with the varnish with a cube applicator so that the dry thickness of the coating was about 30 μm (coating width: 25 mm). The coated film was dried with an air circulation dryer at 105° C. for 5 minutes to provide a sample tape. In the same manner as above, sample tapes were prepared using the resin acid ester compositions of Examples 6 to 8 and Comparative Examples 8 to 14. The adhesive strength, holding power and ball tack of the tapes were measured and the comprehensive evaluation of the ester compositions when used for pressure-sensitive adhesives was carried out in the same manner as in the evaluation of pressure-sensitive adhesive properties of varnish type SIS-based pressure-sensitive adhesives.

TABLE 1

| | | | Example 1 | Example 2 | Example 3 | Example 4 | Example 5 | Example 6 | Example 7 | Example 8 |
|---|---|---|---|---|---|---|---|---|---|---|
| | Resin acid ester composition | | (A1) | (A2) | (A3) | (A4) | (A1) | (A2) | (A3) | (A4) |
| | Amount of resin acid ester of general formula (1) [%] | | 83 | 79 | 87 | 81 | 83 | 79 | 87 | 81 |
| | $S'_{NMR}/S_{NMR}$ ratio [%] | | 8 | 7 | 10 | 7 | 8 | 7 | 10 | 7 |
| | Color tone [H] | | 130 | 100 | 140 | 150 | 130 | 100 | 140 | 150 |
| | Acid value [mg KOH/g] | | 5 | 8 | 3 | 6 | 5 | 8 | 3 | 6 |
| | Hydroxyl value [mg KOH/g] | | 8 | 15 | 5 | 10 | 8 | 15 | 5 | 10 |
| | Softening point [° C.] | | 97 | 93 | 103 | 97 | 97 | 93 | 103 | 97 |
| Hot melt type pressure-sensitive adhesive | Rubber | | SIS | SIS | SIS | SIS | SBS | SBS | SBS | SBS |
| | Melt viscosity [mPa·s] | 200° C. | 7,400 | 8,000 | 6,400 | 7,400 | 9,500 | 10,600 | 8,500 | 11,000 |
| | | 180° C. | 12,000 | 12,400 | 10,400 | 12,800 | 15,400 | 17,000 | 13,600 | 17,600 |
| | | 160° C. | 18,000 | 24,000 | 17,000 | 25,000 | 27,500 | 30,500 | 24,500 | 31,500 |
| | | 140° C. | 42,000 | 48,000 | 36,000 | 53,000 | 60,000 | 67,000 | 54,000 | 69,500 |
| | | 120° C. | 126,000 | 130,000 | 108,000 | 172,000 | 141,000 | 157,000 | 126,000 | 163,000 |
| | Coatability | | A | A | A | A | A | A | A | A |
| | Adhesive strength [N/25 mm] | | 32.6 | 31.2 | 29.9 | 30.0 | 31.8 | 30.4 | 29.0 | 29.2 |
| | Holding power [mm] | | 3.5 | 3.0 | 3.5 | 2.5 | 3.0 | 3.0 | 3.0 | 3.0 |
| | Ball tack [cm] | | 2.8 | 2.5 | 3.1 | 2.8 | 2.8 | 2.7 | 3.5 | 3.0 |
| | Probe tack [N/25 mm ø] | | 6.3 | 6.1 | 6.7 | 6.2 | 8.5 | 8.2 | 9.0 | 8.3 |
| | Evaluation results | | A | A | A | A | A | A | A | A |
| Varnish-type pressure-sensitive adhesive | Rubber | | SIS | SIS | SIS | SIS | SBS | SBS | SBS | SBS |
| | Adhesive strength [N/25 mm] | | 14.8 | 14.1 | 13.5 | 13.6 | 14.4 | 13.7 | 13.1 | 13.2 |
| | Holding power [mm] | | 0.3 | 0.2 | 0.3 | 0.1 | 0.2 | 0.2 | 0.2 | 0.2 |
| | Ball tack [cm] | | 9.8 | 8.6 | 10.8 | 9.7 | 9.7 | 8.6 | 10.9 | 9.7 |
| | Evaluation results | | A | A | A | A | A | A | A | A |

TABLE 2

|  |  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Resin acid ester composition |  |  | (B1) | (B2) | (B3) | (B4) | (B5) | (B6) | (B7) |
| Amount of resin acid ester of general formula (1) [%] |  |  | 74 | 80 | 66 | 57 | 72 | Below detection limit | Below detection limit |
| $S'_{NMR}/S_{NMR}$ ratio [%] |  |  | 5 | 2 | 7 | 3 | 3 | 7 | 7 |
| Color tone [H] |  |  | 100 | 100 | 140 | 90 | 90 | 150 | 400 |
| Acid value [mg KOH/g] |  |  | 9 | 7 | 6 | 5 | 9 | 14 | 14 |
| Hydroxyl value [mg KOH/g] |  |  | 17 | 11 | 25 | 35 | 19 | 30 | 19 |
| Softening point [° C.] |  |  | 93 | 101 | 95 | 87 | 90 | 55 | 115 |
| Hot melt type pressure-sensitive adhesive | Rubber |  | SIS | SIS | SIS | SIS | SIS | SIS | SIS |
|  | Melt viscosity [mPa · s] | 200° C. | 13,200 | 26,000 | 8,200 | 20,400 | 22,000 | 8,000 | 16,000 |
|  |  | 180° C. | 19,000 | 44,000 | 13,200 | 34,000 | 36,000 | 11,400 | 25,000 |
|  |  | 160° C. | 33,000 | 98,000 | 20,000 | 59,000 | 74,000 | 17,600 | 47,500 |
|  |  | 140° C. | 70,000 | Not measurable | 47,000 | 150,000 | Not measurable | 31,200 | 110,000 |
|  |  | 120° C. | Not measurable | Not measurable | 140,000 | Not measurable | Not measurable | 65,000 | Not measurable |
|  | Coatability |  | C | C | A | C | C | A | C |
|  | Adhesive strength [N/25 mm] |  | 25.0 | 24.0 | 24.8 | 25.5 | 25.0 | 11.8 | 31.5 |
|  | Holding power [mm] |  | 3.0 | 0.1 | 5.0 | 6.0 | 3.0 | Dropped | 3.0 |
|  | Ball tack [cm] |  | 3.0 | 4.0 | 2.7 | 3.8 | 3.8 | 1.8 | 3.2 |
|  | Probe tack [N/25 mm ø] |  | 7.1 | 3.2 | 5.3 | 4.5 | 7.1 | 3.6 | 9.6 |
|  | Evaluation results |  | A | B | B | B | A | B | A |
| Varnish-type pressure-sensitive adhesive | Rubber |  | SIS | SIS | SIS | SIS | SIS | SIS | SIS |
|  | Adhesive strength [N/25 mm] |  | 14.3 | 13.8 | 11.6 | 12.2 | 13.6 | 5.5 | 14.3 |
|  | Holding power [mm] |  | 0.2 | 0.1 | 0.6 | 0.7 | 0.2 | Dropped | 0.1 |
|  | Ball tack [cm] |  | 9.8 | 11.0 | 9.9 | 9.0 | 10.0 | 2.4 | 10.2 |
|  | Evaluation results |  | A | A | B | B | A | B | A |

TABLE 3

|  |  |  | Comparative Example 8 | Comparative Example 9 | Comparative Example 10 | Comparative Example 11 | Comparative Example 12 | Comparative Example 13 | Comparative Example 14 |
|---|---|---|---|---|---|---|---|---|---|
| Resin acid ester composition |  |  | (B1) | (B2) | (B3) | (B4) | (B5) | (B6) | (B7) |
| Amount of resin acid ester of general formula (1) [%] |  |  | 74 | 80 | 66 | 57 | 72 | Below detection limit | Below detection limit |
| $S'_{NMR}/S_{NMR}$ ratio [%] |  |  | 5 | 2 | 7 | 3 | 3 | 7 | 7 |
| Color tone [H] |  |  | 100 | 100 | 140 | 90 | 90 | 150 | 400 |
| Acid value [mg KOH/g] |  |  | 9 | 7 | 6 | 5 | 9 | 14 | 14 |
| Hydroxyl value [mg KOH/g] |  |  | 17 | 11 | 25 | 35 | 19 | 30 | 19 |
| Softening point [° C.] |  |  | 93 | 101 | 95 | 87 | 90 | 55 | 115 |
| Hot melt type pressure-sensitive adhesive | Rubber |  | SBS | SBS | SBS | SBS | SBS | SBS | SBS |
|  | Melt viscosity [mPa · s] | 200° C. | 12,600 | 19,400 | 10,900 | 16,000 | 19,400 | 10,600 | 14,300 |
|  |  | 180° C. | 19,800 | 33,000 | 18,200 | 26,400 | 33,000 | 15,600 | 23,200 |
|  |  | 160° C. | 36,000 | 73,500 | 25,500 | 55,000 | 73,500 | 22,400 | 45,500 |
|  |  | 140° C. | 70,500 | Not measurable | 65,500 | 114,000 | Not measurable | 43,500 | 92,000 |
|  |  | 120° C. | Not measurable | Not measurable | 169,000 | Not measurable | Not measurable | 78,500 | Not measurable |
|  | Coatability |  | C | C | A | C | C | A | C |
|  | Adhesive strength [N/25 mm] |  | 25.1 | 16.0 | 22.3 | 26.3 | 25.1 | 13.4 | 31.5 |

TABLE 3-continued

| | | Comparative Example 8 | Comparative Example 9 | Comparative Example 10 | Comparative Example 11 | Comparative Example 12 | Comparative Example 13 | Comparative Example 14 |
|---|---|---|---|---|---|---|---|---|
| | Holding power [mm] | 3.0 | 0.1 | 3.0 | 5.0 | 3.0 | Dropped | 1.0 |
| | Ball tack [cm] | 3.5 | 4.2 | 3.3 | 4.2 | 3.9 | 2.7 | 3.4 |
| | Probe tack [N/25 mm ø] | 11.0 | 4.2 | 13.8 | 3.2 | 11.0 | 5.7 | 15.4 |
| | Evaluation results | A | B | B | B | A | B | A |
| Varnish-type pressure-sensitive adhesive | Rubber | SBS | SBS | SBS | SBS | SBS | SBS | SBS |
| | Adhesive strength [N/25 mm] | 14.4 | 9.2 | 12.0 | 7.4 | 13.7 | 7.0 | 13.6 |
| | Holding power [mm] | 0.2 | 0.1 | 0.2 | 0.5 | 0.2 | Dropped | 0.1 |
| | Ball tack [cm] | 10.2 | 12.8 | 9.9 | 11.0 | 10.4 | 3.3 | 10.8 |
| | Evaluation results | A | B | B | B | A | B | A |

As is revealed from the results of Examples 1 to 8, when an ester composition comprises 70% by weight or more of a resin acid ester represented by the general formula (1) and has at least a 6% S'$_{NMR}$/S$_{NMR}$ ratio, the ester composition not only exhibits an excellent reduction effect on the melt viscosity of the resulting hot melt type pressure-sensitive adhesive composition but also imparts excellent adhesive properties and/or pressure-sensitive adhesive properties.

As is revealed from the results of Comparative Examples 1, 2, 5, 8, 9 and 12, when the S'$_{NMR}$/S$_{NMR}$ ratio of an ester composition is less than 6%, even if the ester composition comprises 70% by weight or more of a resin acid ester represented by the general formula (1), the ester composition cannot exhibit a sufficient reduction effect on the melt viscosity of the resulting hot melt composition even while imparting excellent adhesive properties and/or pressure-sensitive adhesive properties.

As is revealed from the results of Comparative Examples 3 and 10, when the amount of a resin acid ester represented by the general formula (1) in an ester composition is less than 70% by weight, even if the S'$_{NMR}$/S$_{NMR}$ ratio of the ester composition is at least 6%, the ester composition cannot impart sufficient adhesive properties and/or pressure-sensitive adhesive properties even while exhibiting an excellent reduction effect on the melt viscosity of the resulting hot melt composition.

As is revealed from Comparative Examples 4 and 11, when the amount of a resin acid ester represented by the general formula (1) in an ester composition is less than 70% by weight and the S'$_{NMR}$/S$_{NMR}$ ratio is less than 6%, the ester composition neither exhibits a sufficient reduction effect on the melt viscosity nor imparts sufficient adhesive properties and/or pressure-sensitive adhesive properties.

As is revealed from Comparative Examples 6, 7, 13 and 14, when an aliphatic diol or an aliphatic tetraol is used instead of the aliphatic triol to form an ester composition, even if the S'$_{NMR}$/S$_{NMR}$ ratio of the ester composition is at least 6%, the ester composition neither exhibits a sufficient reduction effect on the melt viscosity of the resulting hot melt composition nor imparts sufficient adhesive properties and/or pressure-sensitive adhesive properties.

INDUSTRIAL APPLICABILITY

The present invention can provide a tackifier suitable for medical or industrial use, especially suitable for medical use. The adhesive and/or pressure-sensitive adhesive of the present invention for medical use can be effectively used as a material for, in particular, an adhesive sheet and/or pressure-sensitive adhesive sheet for medical use, such as patches, cataplasms and wet compresses, or an adhesive tape and/or pressure-sensitive adhesive tape for medical use, such as adhesive bandages. The adhesive and/or pressure-sensitive adhesive of the present invention for industrial use can be effectively used as an adhesive for, for example, hygiene products such as paper diapers and sanitary napkins and automotive interior materials.

The invention claimed is:

1. A solvent-free hot melt type adhesive and/or pressure-sensitive adhesive for medical or industrial use, the adhesive comprising
   (1) a tackifier being composed of an ester composition, characterized by
   (i) the ester composition comprising 70% by weight or more of a resin acid ester represented by the general formula (1):

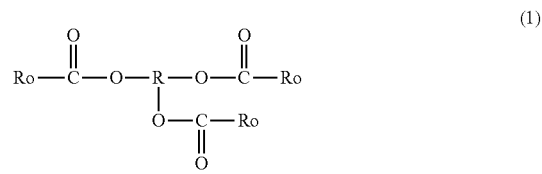

wherein Ro represents a residue of a resin acid and R represents a residue of an aliphatic triol, and
   (ii) the S'$_{NMR}$/S$_{NMR}$ ratio of the ester composition being at least 6% in the $^1$H-NMR spectrum of the ester composition, wherein $_{S'NMR}$ is the total integral value of the proton signal(s) appearing in the region of 6 to 8 ppm and S$_{NMR}$ is the total integral value of all the proton signals appearing over the entire range of the $^1$H-NMR spectrum, and
   (2) a synthetic rubber elastomer.

2. The adhesive and/or pressure-sensitive adhesive according to claim 1, wherein the synthetic rubber elastomer is at least one type selected from the group consisting of styrene-isoprene-styrene block copolymers (SISs), styrenebutadiene-styrene block copolymers (SBSs), styrene-hydrogenated butadiene-styrene block copolymers (SEBSs) and styrene-ethylene/propylene-styrene copolymers (SEPSs).

3. The adhesive and/or pressure-sensitive adhesive according to claim 1, wherein the amount of the tackifier is 50 to 200 parts by weight relative to 100 parts by weight of the synthetic rubber elastomer.

4. The adhesive and/or pressure-sensitive adhesive according to claim 1, wherein a melt viscosity at 200° C. of the adhesive and/or pressure-sensitive adhesive is 1,000 to 20,000 mPa·s when the viscosity is measured with a B-type viscometer.

5. The adhesive and/or pressure-sensitive adhesive according to claim 1, wherein the ester composition has a hydroxyl value of 1 to 20 mg KOH/g.

6. An adhesive sheet and/or pressure-sensitive adhesive sheet for medical or industrial use obtainable using the adhesive and/or pressure-sensitive adhesive according to claim 1.

7. An adhesive tape and/or pressure-sensitive adhesive tape for medical or industrial use obtainable using the adhesive and/or pressure-sensitive adhesive according to claim 1.

* * * * *